US009486368B2

(12) United States Patent
Nelson (10) Patent No.: US 9,486,368 B2
(45) Date of Patent: Nov. 8, 2016

(54) DISPOSABLE HYGIENIC ARTICLE WITH MEANS FOR DIAGNOSTIC TESTING

(71) Applicant: Medline Industries, Inc., Mundelein, IL (US)

(72) Inventor: Christopher Nelson, Hiram, GA (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 14/097,955

(22) Filed: Dec. 5, 2013

(65) Prior Publication Data

US 2015/0157251 A1    Jun. 11, 2015

(51) Int. Cl.
*A61F 13/15* (2006.01)
*A61B 5/145* (2006.01)
*A61B 5/00* (2006.01)
*A61F 13/514* (2006.01)
*A61F 13/84* (2006.01)
*A61B 10/00* (2006.01)
*A61F 13/42* (2006.01)
*A61F 13/45* (2006.01)

(52) U.S. Cl.
CPC ..... *A61F 13/15723* (2013.01); *A61B 5/14507* (2013.01); *A61B 5/6808* (2013.01); *A61B 10/007* (2013.01); *A61F 13/15585* (2013.01); *A61F 13/15699* (2013.01); *A61F 13/15756* (2013.01); *A61F 13/51498* (2013.01); *A61F 13/84* (2013.01); *A61B 2010/0003* (2013.01); *A61B 2562/0295* (2013.01); *A61F 13/42* (2013.01); *A61F 2013/4593* (2013.01); *A61F 2013/51468* (2013.01); *A61F 2013/8473* (2013.01); *Y10T 156/1062* (2015.01)

(58) Field of Classification Search
CPC ......................... A61F 13/42; A61F 2013/4593
USPC .............. 604/385.14, 385.13, 386, 387, 393, 604/394, 395, 396
See application file for complete search history.

(56) References Cited

U.S. PATENT DOCUMENTS

| 688,143 A | 12/1901 | Windle |
| 1,614,239 A | 1/1927 | Hammond |
| RE26,151 E | 1/1967 | Duncan et al. |

(Continued)

FOREIGN PATENT DOCUMENTS

| CN | 102010228 A | 4/2011 |
| CN | 102011336 A | 4/2011 |

(Continued)

OTHER PUBLICATIONS

Bercovici, M. et al. "Rapid Detection of Urinary Tract Infections Using Isotachophoresis and Molecular Beacons." Analytical chemistry 83.11 (2011): 4110-4117. PMC. Web. May 28, 2015. <http://www.ncbi.nlm.nih.gov/pmc/articles/PMC3116659/>.

(Continued)

*Primary Examiner* — Jacqueline Stephens
(74) *Attorney, Agent, or Firm* — Laubscher, Spendlove & Laubscher, P.C.

(57) ABSTRACT

A disposable, wearable article can be used for collecting a sample and performing urinalysis. The article incorporates a test port feature to simplify this function. The test port has a resealable cover that can be used to selectively expose an aperture through the backsheet of the disposable article. The test port is used to position test devices, such as urine test strips to urine collected in the disposable article.

19 Claims, 7 Drawing Sheets

(56) References Cited

U.S. PATENT DOCUMENTS

| | | |
|---|---|---|
| 3,338,992 A | 8/1967 | Kinney |
| 3,341,394 A | 9/1967 | Kinney |
| 3,485,706 A | 12/1969 | Evans |
| 3,502,538 A | 3/1970 | Petersen |
| 3,502,763 A | 3/1970 | Hartmann |
| 3,542,615 A | 11/1970 | Dobo et al. |
| 3,612,055 A | 10/1971 | Mesek et al. |
| 3,692,618 A | 9/1972 | Carduck et al. |
| 3,802,817 A | 4/1974 | Matsuki et al. |
| 3,849,241 A | 11/1974 | Harding et al. |
| 3,860,003 A | 1/1975 | Buell |
| 3,955,575 A | 5/1976 | Okuda |
| 3,994,486 A | 11/1976 | Nystrand |
| 4,050,462 A | 9/1977 | Woon et al. |
| 4,051,853 A | 10/1977 | Egan, Jr. |
| 4,055,180 A | 10/1977 | Karami |
| 4,084,592 A | 4/1978 | Tritsch |
| 4,145,763 A | 3/1979 | Abrams et al. |
| 4,195,634 A | 4/1980 | DiSalvo et al. |
| 4,205,679 A | 6/1980 | Repke et al. |
| 4,246,900 A | 1/1981 | Schroder |
| 4,251,643 A | 2/1981 | Harada et al. |
| 4,253,461 A | 3/1981 | Strickland et al. |
| 4,296,750 A | 10/1981 | Woon et al. |
| 4,317,449 A | 3/1982 | Novakoski |
| 4,340,563 A | 7/1982 | Appel et al. |
| 4,381,781 A | 5/1983 | Sciaraffa et al. |
| 4,402,690 A | 9/1983 | Redfern |
| 4,410,324 A | 10/1983 | Sabee |
| 4,413,996 A | 11/1983 | Taylor |
| 4,500,316 A | 2/1985 | Damico |
| 4,516,976 A | 5/1985 | Bell |
| 4,560,381 A | 12/1985 | Southwell |
| 4,596,568 A | 6/1986 | Flug |
| 4,610,680 A | 9/1986 | LaFleur |
| 4,610,682 A | 9/1986 | Kopp |
| 4,615,695 A | 10/1986 | Cooper |
| 4,639,254 A | 1/1987 | LeGault et al. |
| 4,643,932 A | 2/1987 | Daniels |
| 4,662,875 A | 5/1987 | Hirotsu et al. |
| 4,663,220 A | 5/1987 | Wisneski et al. |
| 4,670,012 A | 6/1987 | Johnson |
| 4,673,402 A | 6/1987 | Weisman et al. |
| 4,680,012 A | 7/1987 | Morley et al. |
| 4,695,278 A | 9/1987 | Lawson |
| 4,699,620 A | 10/1987 | Bernardin |
| 4,699,621 A | 10/1987 | Stevens et al. |
| 4,699,622 A | 10/1987 | Toussant et al. |
| 4,704,116 A | 11/1987 | Enloe |
| 4,705,513 A | 11/1987 | Sheldon et al. |
| 4,710,190 A | 12/1987 | Wood et al. |
| 4,720,415 A | 1/1988 | Vander Wielen et al. |
| 4,753,649 A | 6/1988 | Pazdernik |
| 4,758,241 A | 7/1988 | Papajohn |
| 4,770,656 A | 9/1988 | Proxmire et al. |
| 4,798,603 A | 1/1989 | Meyer et al. |
| 4,834,735 A | 5/1989 | Alemany et al. |
| 4,838,885 A | 6/1989 | Bernardin |
| 4,842,596 A | 6/1989 | Kielpikowski et al. |
| 4,846,815 A | 7/1989 | Scripps |
| 4,869,724 A | 9/1989 | Scripps |
| 4,883,480 A | 11/1989 | Huffman et al. |
| 4,884,323 A | 12/1989 | Provost et al. |
| 4,911,702 A | 3/1990 | O'Leary et al. |
| 4,916,005 A | 4/1990 | Loppert et al. |
| 4,936,840 A | 6/1990 | Proxmire |
| 4,938,753 A | 7/1990 | Van Gompel et al. |
| 4,938,757 A | 7/1990 | Van Gompel et al. |
| 4,940,464 A | 7/1990 | Van Gompel et al. |
| 4,963,140 A | 10/1990 | Robertson et al. |
| 4,964,860 A | 10/1990 | Gipson et al. |
| 4,988,344 A | 1/1991 | Reising et al. |
| 4,988,345 A | 1/1991 | Reising et al. |
| 5,013,382 A | 5/1991 | Nalowaniec et al. |
| 5,019,063 A | 5/1991 | Marsan et al. |
| 5,019,072 A | 5/1991 | Polski |
| 5,019,073 A | 5/1991 | Roessler et al. |
| 5,024,672 A | 6/1991 | Widlund |
| 5,026,446 A | 6/1991 | Johnston et al. |
| 5,034,008 A | 7/1991 | Breitkoph |
| 5,046,272 A | 9/1991 | Vogt et al. |
| 5,047,023 A | 9/1991 | Berg |
| 5,055,103 A | 10/1991 | Nomura et al. |
| 5,061,259 A | 10/1991 | Goldman et al. |
| 5,061,262 A | 10/1991 | Chen et al. |
| 5,062,838 A | 11/1991 | Nalowaniec et al. |
| 5,069,678 A | 12/1991 | Yamamoto et al. |
| 5,087,253 A | 2/1992 | Cooper |
| 5,104,116 A | 4/1992 | Pohjola |
| 5,106,385 A | 4/1992 | Allen et al. |
| 5,108,384 A | 4/1992 | Goulait |
| 5,128,193 A | 7/1992 | Anapol et al. |
| 5,133,707 A | 7/1992 | Rogers et al. |
| 5,134,007 A | 7/1992 | Reising et al. |
| 5,147,343 A | 9/1992 | Kellenberger |
| 5,147,347 A | 9/1992 | Huang |
| 5,149,334 A | 9/1992 | Lahman et al. |
| 5,149,335 A | 9/1992 | Kellenberger et al. |
| 5,151,092 A | 9/1992 | Buell et al. |
| 5,156,793 A | 10/1992 | Buell et al. |
| 5,156,902 A | 10/1992 | Pieper et al. |
| 5,163,932 A | 11/1992 | Nomura et al. |
| 5,176,668 A | 1/1993 | Bernardin |
| 5,176,670 A | 1/1993 | Roessler et al. |
| 5,176,671 A | 1/1993 | Roessler et al. |
| 5,188,624 A | 2/1993 | Young, Sr. et al. |
| 5,188,627 A | 2/1993 | Igaue et al. |
| 5,192,506 A | 3/1993 | Kureshy et al. |
| 5,219,646 A | 6/1993 | Gallegher et al. |
| 5,224,405 A | 7/1993 | Pohjola |
| 5,226,992 A | 7/1993 | Morman |
| 5,234,422 A | 8/1993 | Sneller et al. |
| 5,235,515 A | 8/1993 | Ungpiyakul et al. |
| 5,236,429 A | 8/1993 | Widlund |
| 5,242,436 A | 9/1993 | Weil et al. |
| 5,246,433 A | 9/1993 | Hasse et al. |
| 5,248,309 A | 9/1993 | Serbiak et al. |
| 5,263,949 A | 11/1993 | Karami et al. |
| 5,275,588 A | 1/1994 | Matsumoto et al. |
| 5,275,590 A | 1/1994 | Huffman et al. |
| 5,279,604 A | 1/1994 | Robertson et al. |
| 5,286,543 A | 2/1994 | Ungpiyakul et al. |
| 5,288,546 A | 2/1994 | Roessler et al. |
| 5,294,478 A | 3/1994 | Wanek et al. |
| 5,295,988 A | 3/1994 | Muckenfuhs et al. |
| 5,300,057 A | 4/1994 | Miller et al. |
| 5,304,161 A | 4/1994 | Noel et al. |
| 5,304,162 A | 4/1994 | Kuen |
| 5,318,555 A | 6/1994 | Siebers et al. |
| 5,320,531 A | 6/1994 | Delizo-Madamba |
| 5,326,612 A | 7/1994 | Goulait |
| 5,330,458 A | 7/1994 | Buell et al. |
| 5,344,691 A | 9/1994 | Hanschen et al. |
| 5,348,547 A | 9/1994 | Payne et al. |
| 5,350,370 A | 9/1994 | Jackson et al. |
| 5,358,500 A | 10/1994 | Lavon |
| 5,364,382 A | 11/1994 | Latimer et al. |
| 5,370,634 A | 12/1994 | Ando et al. |
| 5,370,639 A | 12/1994 | Widlund |
| 5,383,872 A | 1/1995 | Roessler et al. |
| 5,387,208 A | 2/1995 | Ashton et al. |
| 5,399,219 A | 3/1995 | Roessier et al. |
| 5,403,302 A | 4/1995 | Roessier et al. |
| 5,411,497 A | 5/1995 | Tanzer et al. |
| 5,422,172 A | 6/1995 | Wu |
| 5,423,789 A | 6/1995 | Kuen |
| 5,425,377 A | 6/1995 | Caillouette |
| 5,425,725 A | 6/1995 | Tanzer et al. |
| 5,433,715 A | 7/1995 | Tanzer et al. |
| 5,439,458 A | 8/1995 | Noel et al. |
| 5,458,592 A | 10/1995 | Abuto et al. |
| 5,460,622 A | 10/1995 | Dragoo et al. |
| 5,462,541 A | 10/1995 | Bruemmer et al. |
| 5,466,513 A | 11/1995 | Wanek et al. |

(56) References Cited

U.S. PATENT DOCUMENTS

| | | |
|---|---|---|
| 5,468,236 A | 11/1995 | Everhart et al. |
| 5,486,167 A | 1/1996 | Dragoo et al. |
| 5,489,282 A | 2/1996 | Zehner et al. |
| 5,490,846 A | 2/1996 | Ellis et al. |
| 5,496,298 A | 3/1996 | Kuepper et al. |
| 5,496,428 A | 3/1996 | Sageser et al. |
| 5,501,679 A | 3/1996 | Krueger et al. |
| 5,507,895 A | 4/1996 | Suekane |
| 5,509,914 A | 4/1996 | Osborn, III |
| 5,509,915 A | 4/1996 | Hanson et al. |
| 5,527,300 A | 6/1996 | Sauer |
| 5,527,302 A | 6/1996 | Endres et al. |
| 5,527,304 A | 6/1996 | Buell et al. |
| 5,527,305 A | 6/1996 | Goulait et al. |
| 5,537,722 A | 7/1996 | Neiderhofer et al. |
| 5,540,796 A | 7/1996 | Fries |
| 5,549,591 A | 8/1996 | Landvogt |
| 5,549,592 A | 8/1996 | Fries et al. |
| 5,554,243 A | 9/1996 | Igaue et al. |
| 5,556,394 A | 9/1996 | Roe et al. |
| 5,560,798 A | 10/1996 | Brusky |
| 5,562,646 A | 10/1996 | Goldman et al. |
| 5,562,650 A | 10/1996 | Everett et al. |
| 5,569,229 A * | 10/1996 | Rogers ............... 604/385.09 |
| 5,571,096 A | 11/1996 | Dobrin et al. |
| 5,575,782 A | 11/1996 | Hasse et al. |
| 5,591,151 A | 1/1997 | Hasse et al. |
| 5,593,399 A | 1/1997 | Tanzer et al. |
| 5,595,567 A | 1/1997 | King et al. |
| 5,595,618 A | 1/1997 | Fries et al. |
| 5,599,335 A | 2/1997 | Goldman et al. |
| 5,599,620 A | 2/1997 | Huskey |
| 5,601,542 A | 2/1997 | Melius et al. |
| 5,603,707 A | 2/1997 | Trombetta et al. |
| 5,605,735 A | 2/1997 | Zehner et al. |
| 5,624,423 A | 4/1997 | Anjur et al. |
| 5,624,428 A | 4/1997 | Sauer |
| 5,624,429 A | 4/1997 | Long et al. |
| 5,628,741 A | 5/1997 | Buell et al. |
| 5,629,063 A | 5/1997 | Gobran |
| 5,634,917 A | 6/1997 | Fujioka et al. |
| 5,647,864 A | 7/1997 | Allen et al. |
| 5,659,538 A | 8/1997 | Stuebe et al. |
| 5,660,666 A | 8/1997 | Dilnik et al. |
| 5,669,894 A | 9/1997 | Goldman et al. |
| 5,669,900 A | 9/1997 | Bullwinkel et al. |
| 5,674,216 A | 10/1997 | Buell et al. |
| 5,681,300 A | 10/1997 | Ahr et al. |
| 5,683,533 A | 11/1997 | Keighley et al. |
| 5,683,794 A | 11/1997 | Wadsworth et al. |
| 5,685,873 A | 11/1997 | Bruemmer et al. |
| 5,690,628 A | 11/1997 | Huskey et al. |
| 5,706,524 A | 1/1998 | Herrin et al. |
| 5,718,698 A | 2/1998 | Dobrin et al. |
| 5,722,127 A | 3/1998 | Coates |
| 5,735,839 A | 4/1998 | Kawaguchi et al. |
| 5,735,840 A | 4/1998 | Kline et al. |
| 5,738,669 A | 4/1998 | Suzuki et al. |
| 5,741,241 A | 4/1998 | Guidotti et al. |
| 5,745,922 A | 5/1998 | Rajala et al. |
| 5,746,731 A | 5/1998 | Hisada |
| 5,749,865 A | 5/1998 | Yamamoto et al. |
| 5,749,866 A | 5/1998 | Roe et al. |
| 5,760,080 A | 6/1998 | Wada et al. |
| 5,769,838 A | 6/1998 | Buell et al. |
| 5,772,649 A | 6/1998 | Siudzinski |
| 5,779,831 A | 7/1998 | Schmitz |
| 5,785,699 A | 7/1998 | Schmitz |
| 5,795,350 A | 8/1998 | Schmitz |
| 5,797,893 A | 8/1998 | Wada et al. |
| 5,817,400 A | 10/1998 | Chen et al. |
| 5,820,617 A | 10/1998 | Igaue et al. |
| 5,830,206 A | 11/1998 | Larsson |
| 5,843,056 A | 12/1998 | Good et al. |
| 5,843,066 A | 12/1998 | Dobrin |
| 5,843,067 A | 12/1998 | Trombetta et al. |
| 5,843,575 A | 12/1998 | Wang et al. |
| 5,849,000 A | 12/1998 | Anjur et al. |
| 5,853,402 A | 12/1998 | Faulks et al. |
| 5,855,574 A | 1/1999 | Kling et al. |
| 5,858,515 A | 1/1999 | Stokes et al. |
| 5,858,535 A | 1/1999 | Wang et al. |
| 5,860,964 A | 1/1999 | Willekens et al. |
| 5,861,074 A | 1/1999 | Wu |
| 5,865,823 A | 2/1999 | Curro |
| 5,876,392 A | 3/1999 | Hisada |
| 5,876,531 A | 3/1999 | Jacobs et al. |
| 5,895,379 A | 4/1999 | Litchholt et al. |
| 5,897,545 A | 4/1999 | Kline et al. |
| 5,897,546 A | 4/1999 | Kido et al. |
| 5,902,296 A | 5/1999 | Fluyeras |
| 5,904,793 A | 5/1999 | Gorman et al. |
| 5,906,604 A | 5/1999 | Ronnberg et al. |
| 5,916,206 A | 6/1999 | Otsubo et al. |
| 5,919,178 A | 7/1999 | Widlund |
| 5,926,926 A | 7/1999 | Kato |
| 5,928,212 A | 7/1999 | Kline et al. |
| 5,940,887 A | 8/1999 | Rajala et al. |
| 5,941,865 A | 8/1999 | Otsubo et al. |
| 5,948,507 A | 9/1999 | Chen et al. |
| 5,957,906 A | 9/1999 | Roe et al. |
| 5,961,506 A | 10/1999 | Guidotti et al. |
| 5,961,761 A | 10/1999 | Heindel et al. |
| 5,971,970 A | 10/1999 | Carlbark et al. |
| 5,977,430 A | 11/1999 | Roe et al. |
| 5,984,911 A | 11/1999 | Siebers et al. |
| 6,007,527 A | 12/1999 | Kawaguchi et al. |
| 6,011,196 A | 1/2000 | Wang et al. |
| 6,017,621 A | 1/2000 | Hilston et al. |
| 6,020,535 A | 2/2000 | Blenke et al. |
| 6,030,373 A | 2/2000 | Van Gompel et al. |
| 6,036,805 A | 3/2000 | McNichols |
| 6,045,543 A | 4/2000 | Pozniak et al. |
| 6,049,915 A | 4/2000 | Malowaniec |
| 6,049,916 A | 4/2000 | Rajala et al. |
| 6,051,094 A | 4/2000 | Melbye et al. |
| 6,063,067 A | 5/2000 | Takizawa et al. |
| 6,066,774 A * | 5/2000 | Roe ............... A61F 13/42 604/358 |
| 6,068,620 A | 5/2000 | Chmielewski |
| 6,075,178 A | 6/2000 | La Wilhelm et al. |
| 6,077,379 A | 6/2000 | Herrin et al. |
| 6,080,909 A | 6/2000 | Osterdahl et al. |
| 6,083,212 A | 7/2000 | Kumasaka |
| 6,093,869 A | 7/2000 | Roe et al. |
| 6,098,203 A | 8/2000 | Rajala et al. |
| 6,107,538 A | 8/2000 | Young et al. |
| 6,107,539 A | 8/2000 | Palumbo et al. |
| 6,117,121 A | 9/2000 | Faulks et al. |
| 6,132,411 A | 10/2000 | Huber et al. |
| 6,140,551 A | 10/2000 | Niemeyer et al. |
| 6,142,986 A | 11/2000 | Lord et al. |
| 6,149,590 A | 11/2000 | Smith et al. |
| 6,149,636 A | 11/2000 | Roe et al. |
| 6,156,024 A | 12/2000 | Schulte et al. |
| 6,159,584 A | 12/2000 | Eaton et al. |
| 6,179,820 B1 | 1/2001 | Fernfors |
| 6,191,055 B1 | 2/2001 | Boyer, III et al. |
| 6,197,012 B1 | 3/2001 | Mishima et al. |
| 6,198,018 B1 | 3/2001 | Curro |
| 6,203,496 B1 | 3/2001 | Gael et al. |
| 6,213,991 B1 | 4/2001 | Kling et al. |
| 6,213,992 B1 | 4/2001 | Dreier |
| 6,218,593 B1 | 4/2001 | Torimae et al. |
| 6,222,091 B1 | 4/2001 | Beihoffer et al. |
| 6,224,961 B1 | 5/2001 | Hsueh et al. |
| 6,235,011 B1 | 5/2001 | O'Connell |
| 6,240,569 B1 | 6/2001 | Van Gompel et al. |
| 6,241,713 B1 | 6/2001 | Gross et al. |
| 6,255,236 B1 | 7/2001 | Cree et al. |
| 6,258,077 B1 | 7/2001 | Buell et al. |
| 6,260,211 B1 | 7/2001 | Rajala et al. |
| 6,264,643 B1 | 7/2001 | Toyoda |
| 6,266,557 B1 | 7/2001 | Roe et al. |

(56) References Cited

U.S. PATENT DOCUMENTS

| | | |
|---|---|---|
| 6,287,286 B1 | 9/2001 | Akin et al. |
| 6,287,287 B1 | 9/2001 | Eisberg |
| 6,307,119 B1 | 10/2001 | Cammarota et al. |
| 6,307,120 B1 | 10/2001 | Glaug |
| 6,312,420 B1 | 11/2001 | Sasaki et al. |
| 6,315,765 B1 | 11/2001 | Datta et al. |
| 6,328,725 B2 | 12/2001 | Femfors |
| 6,359,192 B1 | 3/2002 | Schmidt et al. |
| 6,364,863 B1 | 4/2002 | Yamamoto et al. |
| 6,367,089 B2 | 4/2002 | Van Gompel et al. |
| 6,368,312 B1 | 4/2002 | Otsubo et al. |
| 6,369,292 B1 | 4/2002 | Strack et al. |
| 6,371,951 B1 | 4/2002 | Koczab et al. |
| 6,372,951 B1 | 4/2002 | Ter-Ovanesyan et al. |
| 6,375,646 B1 | 4/2002 | Widlund et al. |
| 6,383,960 B1 | 5/2002 | Everett et al. |
| 6,392,116 B1 | 5/2002 | Beihoffer et al. |
| 6,394,991 B1 | 5/2002 | Takei et al. |
| 6,395,115 B1 | 5/2002 | Popp et al. |
| 6,395,955 B1 | 5/2002 | Roe et al. |
| 6,399,853 B1 | 6/2002 | Roe et al. |
| 6,402,730 B1 | 6/2002 | Malowaniec |
| 6,407,308 B1 | 6/2002 | Roe et al. |
| 6,409,858 B1 | 6/2002 | Popp et al. |
| 6,413,249 B1 | 7/2002 | Turi et al. |
| 6,414,216 B1 | 7/2002 | Malowaniec |
| 6,423,046 B1 | 7/2002 | Fujioka et al. |
| 6,428,525 B1 | 8/2002 | Malowaniec |
| 6,428,526 B1 | 8/2002 | Heindel et al. |
| 6,429,352 B1 | 8/2002 | Herrlein et al. |
| 6,432,098 B1 | 8/2002 | Kline et al. |
| 6,432,243 B1 | 8/2002 | Popp et al. |
| 6,432,248 B1 | 8/2002 | Popp et al. |
| 6,433,244 B1 | 8/2002 | Roe et al. |
| 6,437,213 B1 | 8/2002 | Schmidt et al. |
| 6,437,214 B1 | 8/2002 | Everett et al. |
| 6,440,117 B1 | 8/2002 | Itoh et al. |
| 6,447,497 B1 | 9/2002 | Olson |
| 6,447,628 B1 | 9/2002 | Couillard et al. |
| 6,448,202 B1 | 9/2002 | Miyazawa et al. |
| 6,454,751 B1 | 9/2002 | Olson |
| 6,455,753 B1 | 9/2002 | Giaug et al. |
| 6,458,115 B1 | 10/2002 | Lindqvist et al. |
| 6,461,343 B1 | 10/2002 | Schaefer et al. |
| 6,461,344 B1 | 10/2002 | Widlund et al. |
| 6,463,633 B1 | 10/2002 | Sangani et al. |
| 6,463,663 B1 | 10/2002 | Kanzawa |
| 6,464,635 B1 | 10/2002 | Jimenez Cerrato et al. |
| 6,465,379 B1 | 10/2002 | Cook et al. |
| D465,842 S | 11/2002 | Magee et al. |
| 6,476,289 B1 | 11/2002 | Buell et al. |
| 6,478,786 B1 | 11/2002 | Glaug et al. |
| 6,479,727 B1 | 11/2002 | Roe |
| 6,481,362 B2 | 11/2002 | Hietpas et al. |
| 6,494,873 B2 | 12/2002 | Karlsson et al. |
| 6,497,032 B2 | 12/2002 | Maxton et al. |
| 6,498,283 B1 | 12/2002 | Wada et al. |
| 6,498,953 B2 | 12/2002 | Roe et al. |
| 6,500,163 B2 | 12/2002 | Rönnberg et al. |
| 6,506,394 B1 | 1/2003 | Yahiaoui et al. |
| 6,506,959 B2 | 1/2003 | Hamajima et al. |
| 6,509,513 B2 | 1/2003 | Glaug et al. |
| 6,513,221 B2 | 2/2003 | Vogt et al. |
| 6,514,187 B2 | 2/2003 | Coenen et al. |
| 6,524,294 B1 | 2/2003 | Hilston et al. |
| 6,533,879 B2 | 3/2003 | Quereshi et al. |
| 6,540,731 B2 | 4/2003 | Magnussson et al. |
| 6,544,244 B1 | 4/2003 | Glaug et al. |
| 6,551,295 B1 | 4/2003 | Schmidt et al. |
| 6,566,578 B1 | 5/2003 | Glaug et al. |
| 6,569,139 B1 | 5/2003 | Datta et al. |
| 6,570,053 B2 | 5/2003 | Roe et al. |
| 6,570,058 B1 | 5/2003 | Fuchs et al. |
| 6,572,595 B1 | 6/2003 | Klemp et al. |
| 6,575,949 B1 | 6/2003 | Waksmundzki et al. |
| 6,575,952 B2 | 6/2003 | Kirk et al. |
| 6,579,275 B1 | 6/2003 | Pozniak et al. |
| 6,582,543 B1 | 6/2003 | Nilsson et al. |
| 6,590,136 B1 | 7/2003 | Young et al. |
| 6,595,976 B2 | 7/2003 | Jitoe et al. |
| 6,596,113 B2 | 7/2003 | Csida et al. |
| 6,602,238 B1 | 8/2003 | Takei et al. |
| 6,605,447 B2 | 8/2003 | Weiss et al. |
| 6,610,904 B1 | 8/2003 | Thomas et al. |
| 6,613,032 B2 | 9/2003 | Ronnberg et al. |
| 6,623,576 B2 | 9/2003 | Mitchell et al. |
| 6,626,881 B2 | 9/2003 | Shingu et al. |
| 6,626,882 B2 | 9/2003 | Hjorth |
| 6,627,394 B2 | 9/2003 | Kritzman et al. |
| 6,630,611 B1 | 10/2003 | Malowaniec |
| 6,632,209 B1 | 10/2003 | Chmielewski |
| 6,635,041 B1 | 10/2003 | Popp et al. |
| 6,635,135 B2 | 10/2003 | Kuen et al. |
| 6,642,431 B1 | 11/2003 | Gellerstedt et al. |
| 6,645,338 B1 | 11/2003 | Sangani et al. |
| 6,646,179 B1 | 11/2003 | Melius et al. |
| 6,646,180 B1 | 11/2003 | Chmielewski |
| 6,648,870 B2 | 11/2003 | Itoh et al. |
| 6,648,871 B2 | 11/2003 | Kusibojoska et al. |
| 6,649,810 B1 | 11/2003 | Minato et al. |
| 6,664,439 B1 | 12/2003 | Arndt et al. |
| 6,669,678 B2 | 12/2003 | Hermansson et al. |
| 6,676,645 B1 | 1/2004 | Bitterhof |
| 6,689,934 B2 | 2/2004 | Dodge, II et al. |
| 6,692,477 B2 | 2/2004 | Gibbs |
| 6,700,036 B2 | 3/2004 | Thomas et al. |
| 6,702,798 B2 | 3/2004 | Christoffel et al. |
| 6,709,423 B1 | 3/2004 | Herrlein et al. |
| 6,710,225 B1 | 3/2004 | Everett et al. |
| 6,713,660 B1 | 3/2004 | Roe et al. |
| 6,719,744 B2 | 4/2004 | Kinnear et al. |
| 6,723,035 B2 | 4/2004 | Franklin et al. |
| 6,726,669 B2 | 4/2004 | Shimada et al. |
| 6,726,670 B2 | 4/2004 | Almberg et al. |
| 6,727,403 B1 | 4/2004 | Ehrnsperger et al. |
| 6,733,483 B2 | 5/2004 | Raufman et al. |
| 6,736,804 B1 | 5/2004 | Robertson et al. |
| 6,740,071 B2 | 5/2004 | Gibbs |
| 6,749,860 B2 | 6/2004 | Tyrrell et al. |
| 6,755,808 B2 | 6/2004 | Balogh et al. |
| 6,761,711 B1 | 7/2004 | Fletcher et al. |
| 6,764,479 B2 | 7/2004 | Kusibojoska et al. |
| 6,770,065 B1 | 8/2004 | Sasaki et al. |
| 6,776,316 B2 | 8/2004 | Van Eperen et al. |
| 6,780,173 B2 | 8/2004 | Mishima et al. |
| 6,780,272 B2 | 8/2004 | Wood |
| 6,790,798 B1 | 9/2004 | Suzuki et al. |
| 6,803,496 B2 | 10/2004 | Elder et al. |
| 6,838,591 B2 | 1/2005 | Waksmundzki et al. |
| 6,840,928 B2 | 1/2005 | Datta et al. |
| 6,846,374 B2 | 1/2005 | Popp et al. |
| 6,849,067 B2 | 2/2005 | Fletcher et al. |
| 6,878,223 B2 | 4/2005 | Kuen et al. |
| 6,885,451 B2 | 4/2005 | Vogt et al. |
| 6,888,043 B2 | 5/2005 | Geiser et al. |
| 6,888,044 B2 | 5/2005 | Fell et al. |
| 6,888,143 B2 | 5/2005 | Vogt et al. |
| 6,891,080 B2 | 5/2005 | Minato et al. |
| 6,904,865 B2 | 6/2005 | Klofta et al. |
| 6,911,024 B2 | 6/2005 | Kusibojoska et al. |
| 6,921,647 B2 | 7/2005 | Kritzman et al. |
| 6,923,798 B2 | 8/2005 | Hedén et al. |
| 6,936,129 B2 | 8/2005 | Karami et al. |
| 6,945,968 B2 | 9/2005 | Svensson et al. |
| 6,946,585 B2 | 9/2005 | Brown |
| 6,953,452 B2 | 10/2005 | Popp et al. |
| 6,955,668 B2 | 10/2005 | Almberg et al. |
| 6,972,011 B2 | 12/2005 | Maeda et al. |
| 6,972,012 B1 | 12/2005 | Pozniak et al. |
| 6,981,951 B1 | 1/2006 | Rahe |
| 6,981,968 B2 | 1/2006 | Kusibojoska et al. |
| 6,991,622 B2 | 1/2006 | Nakaoka et al. |
| 6,994,761 B2 | 2/2006 | Klemp et al. |
| 7,000,260 B2 | 2/2006 | Rajala et al. |

(56) References Cited

U.S. PATENT DOCUMENTS

| | | |
|---|---|---|
| 7,001,368 B2 | 2/2006 | Otsubo |
| 7,002,054 B2 | 2/2006 | Allen et al. |
| 7,018,369 B2 | 3/2006 | Van Gompel et al. |
| 7,044,133 B2 | 5/2006 | Lohrengel et al. |
| 7,048,725 B2 | 5/2006 | Kling et al. |
| 7,060,058 B2 | 6/2006 | Otsubo et al. |
| D527,102 S | 8/2006 | Mills et al. |
| 7,087,046 B2 | 8/2006 | Van Gompel et al. |
| 7,090,667 B2 | 8/2006 | Fell et al. |
| D527,818 S | 9/2006 | Mills et al. |
| 7,156,939 B2 | 1/2007 | Vogt et al. |
| 7,163,745 B2 | 1/2007 | Mangold et al. |
| 7,166,094 B2 | 1/2007 | Glaug et al. |
| 7,172,585 B2 | 2/2007 | Sandin et al. |
| 7,175,910 B2 | 2/2007 | Ehrnsperger et al. |
| 7,195,622 B2 | 3/2007 | Lindström |
| 7,201,743 B2 | 4/2007 | Röhrl |
| 7,204,907 B2 | 4/2007 | Cree et al. |
| 7,217,261 B2 | 5/2007 | Otsubo et al. |
| 7,241,627 B2 | 7/2007 | Wilhelm et al. |
| 7,270,881 B2 | 9/2007 | Schmidt et al. |
| 7,285,178 B2 | 10/2007 | Mischler et al. |
| 7,314,465 B2 | 1/2008 | Van Gompel et al. |
| 7,314,752 B2 | 1/2008 | Kritzman et al. |
| 7,322,967 B2 | 1/2008 | Kondo |
| 7,331,946 B2 | 2/2008 | Shimada et al. |
| 7,332,642 B2 | 2/2008 | Liu |
| 7,344,525 B2 | 3/2008 | Linker, III et al. |
| 7,347,846 B2 | 3/2008 | Hermansson et al. |
| 7,365,238 B2 | 4/2008 | Diehl et al. |
| 7,368,027 B2 | 5/2008 | Schneider et al. |
| 7,373,698 B2 | 5/2008 | Erdman et al. |
| 7,378,567 B2 | 5/2008 | Mangold |
| 7,378,568 B2 | 5/2008 | Thomas et al. |
| 7,387,148 B2 | 6/2008 | Vogt et al. |
| 7,396,349 B2 | 7/2008 | Van Himbergen et al. |
| 7,396,585 B2 | 7/2008 | Schmidt et al. |
| 7,402,339 B2 | 7/2008 | Schmidt et al. |
| 7,411,110 B2 | 8/2008 | Sawyer et al. |
| 7,425,242 B2 | 9/2008 | Olsson et al. |
| 7,432,413 B2 | 10/2008 | Roe et al. |
| 7,435,245 B2 | 10/2008 | Wendelstorf et al. |
| 7,438,709 B2 | 10/2008 | Karami et al. |
| 7,449,014 B2 | 11/2008 | Oba et al. |
| 7,455,665 B2 | 11/2008 | Wendelstorf et al. |
| 7,462,754 B2 | 12/2008 | Malowaniec |
| 7,462,756 B2 | 12/2008 | Malowaniec |
| 7,482,505 B2 | 1/2009 | Stupperich et al. |
| 7,488,535 B2 | 2/2009 | Ehrnsperger et al. |
| 7,504,235 B2 | 3/2009 | Song |
| 7,524,313 B2 | 4/2009 | Kline et al. |
| 7,524,449 B2 | 4/2009 | Walsh et al. |
| 7,524,561 B2 | 4/2009 | Schmidt et al. |
| 7,527,618 B2 | 5/2009 | Benning et al. |
| 7,534,237 B2 | 5/2009 | Olson et al. |
| 7,541,177 B2 | 6/2009 | Kritzman et al. |
| 7,544,628 B2 | 6/2009 | Stupperich et al. |
| 7,559,124 B2 | 7/2009 | Poulakis |
| 7,569,039 B2 | 8/2009 | Matsuda et al. |
| 7,569,041 B2 | 8/2009 | Stupperich et al. |
| 7,592,020 B2 | 9/2009 | Boga et al. |
| 7,604,624 B2 | 10/2009 | Veith et al. |
| 7,621,901 B2 | 11/2009 | Karami |
| 7,682,349 B2 | 3/2010 | Popp et al. |
| 7,687,680 B2 | 3/2010 | Fell et al. |
| 7,695,464 B2 | 4/2010 | Fletcher et al. |
| 7,699,825 B2 | 4/2010 | Nakagawa et al. |
| 7,713,371 B2 | 5/2010 | Lohrengel et al. |
| 7,718,021 B2 | 5/2010 | Venturino et al. |
| 7,722,590 B2 | 5/2010 | Tsuji et al. |
| 7,737,324 B2 | 6/2010 | LaVon et al. |
| 7,744,576 B2 | 6/2010 | Busam et al. |
| 7,744,713 B2 | 6/2010 | Blessing et al. |
| 7,749,211 B2 | 7/2010 | Van Gompel et al. |
| 7,750,203 B2 | 7/2010 | Becker et al. |
| 7,758,558 B2 | 7/2010 | Otsubo |
| 7,794,442 B2 | 9/2010 | Roehrl et al. |
| 7,794,839 B2 | 9/2010 | Schmidt et al. |
| 7,807,861 B2 | 10/2010 | Molander et al. |
| 7,819,851 B2 | 10/2010 | Karlsson |
| 7,837,662 B2 | 11/2010 | Nakagawa et al. |
| 7,838,721 B2 | 11/2010 | Chen |
| 7,838,722 B2 | 11/2010 | Blessing et al. |
| 7,846,383 B2 | 12/2010 | Song |
| 7,851,667 B2 | 12/2010 | Becker et al. |
| 7,851,669 B2 | 12/2010 | Nakagawa et al. |
| 7,857,801 B2 | 12/2010 | Hamall et al. |
| 7,863,498 B2 | 1/2011 | Roe et al. |
| 7,867,213 B2 | 1/2011 | Bandorf et al. |
| 7,906,065 B1 | 3/2011 | Brown et al. |
| 7,918,959 B2 | 4/2011 | Hornung et al. |
| 7,923,597 B2 | 4/2011 | Ponomarenko et al. |
| 7,935,299 B2 | 5/2011 | Walsh et al. |
| 7,943,537 B2 | 5/2011 | Vincent et al. |
| 7,947,467 B2 | 5/2011 | Kritzman et al. |
| 7,947,865 B2 | 5/2011 | Fossum et al. |
| 7,956,236 B2 | 6/2011 | Ponomarenko et al. |
| 7,982,088 B2 | 7/2011 | Roe et al. |
| 7,993,320 B2 | 8/2011 | Hornung et al. |
| 7,994,384 B2 | 8/2011 | Qin et al. |
| 8,016,806 B2 | 9/2011 | Hornung et al. |
| 8,017,827 B2 | 9/2011 | Hundorf et al. |
| 8,025,652 B2 | 9/2011 | Hornung et al. |
| 8,038,662 B2 | 10/2011 | Hornung et al. |
| 8,043,272 B2 | 10/2011 | Long et al. |
| 8,044,257 B2 | 10/2011 | Song |
| 8,083,724 B2 | 12/2011 | Bittner et al. |
| 8,088,967 B2 | 1/2012 | Underhill et al. |
| 8,100,173 B2 | 1/2012 | Hornung et al. |
| 8,138,388 B2 | 3/2012 | Elder et al. |
| 8,142,590 B2 | 3/2012 | Rejala et al. |
| 8,148,598 B2 | 4/2012 | Tsang et al. |
| 8,152,788 B2 | 4/2012 | Beckert et al. |
| 8,158,848 B2 | 4/2012 | Swerev et al. |
| 8,162,913 B2 | 4/2012 | Goates et al. |
| 8,180,603 B2 | 5/2012 | Blessing et al. |
| 8,187,240 B2 | 5/2012 | Busam et al. |
| 8,196,809 B2 | 6/2012 | Thorstensson |
| 8,202,390 B2 | 6/2012 | Malowaniec |
| 8,206,365 B2 | 6/2012 | Norrby |
| 8,206,533 B2 | 6/2012 | Hundorf et al. |
| 8,217,217 B2 | 7/2012 | Diehl et al. |
| 8,221,372 B2 | 7/2012 | Kouno et al. |
| 8,221,379 B2 | 7/2012 | Lam et al. |
| 8,221,672 B2 | 7/2012 | Brown et al. |
| 8,231,593 B2 | 7/2012 | Nakagawa et al. |
| 8,241,263 B2 | 8/2012 | Mills |
| 8,251,967 B2 | 8/2012 | Malowaniec |
| 8,258,366 B2 | 9/2012 | Wendelstorf |
| 8,263,820 B2 | 9/2012 | Carlucci et al. |
| 8,282,617 B2 | 10/2012 | Kaneda |
| 8,292,865 B2 | 10/2012 | Hutson et al. |
| 8,293,967 B2 * | 10/2012 | Klofta et al. .................. 604/361 |
| 8,298,205 B2 | 10/2012 | Norrby et al. |
| 8,303,562 B2 | 11/2012 | Hornung et al. |
| 8,319,005 B2 | 11/2012 | Becker et al. |
| 8,343,296 B2 | 1/2013 | Blessing et al. |
| 8,353,891 B2 | 1/2013 | Hornung et al. |
| 8,454,572 B2 | 6/2013 | Roe et al. |
| 8,454,782 B2 | 6/2013 | Ostertag |
| 8,466,336 B2 | 6/2013 | Carlucci et al. |
| 8,476,173 B2 | 7/2013 | Dovertie et al. |
| 8,496,637 B2 | 7/2013 | Hundorf et al. |
| 8,512,305 B2 | 8/2013 | Dziezok et al. |
| 8,518,539 B2 | 8/2013 | Meyer et al. |
| 8,552,252 B2 | 10/2013 | Hundorf et al. |
| 8,562,580 B2 | 10/2013 | Van Gompel et al. |
| 8,562,581 B2 | 10/2013 | Karami et al. |
| 8,585,666 B2 | 11/2013 | Weisman et al. |
| 8,616,867 B2 | 12/2013 | Brown et al. |
| 8,622,984 B2 | 1/2014 | Rajala et al. |
| 8,663,186 B2 | 3/2014 | Lam et al. |
| 8,668,975 B2 | 3/2014 | Westwood |
| 8,672,915 B2 | 3/2014 | Kuwano et al. |

(56) References Cited

U.S. PATENT DOCUMENTS

| | | |
|---|---|---|
| 8,708,990 B2 | 4/2014 | Beckert et al. |
| 8,747,379 B2 | 6/2014 | Fletcher et al. |
| 8,771,249 B2 | 7/2014 | Beckert et al. |
| 8,784,398 B2 | 7/2014 | Beckert et al. |
| 8,864,733 B2 | 10/2014 | Koenig et al. |
| 8,920,399 B2 | 12/2014 | Mills |
| 2001/0023341 A1 | 9/2001 | Karami |
| 2001/0025147 A1 | 9/2001 | Roe et al. |
| 2001/0034512 A1 | 10/2001 | Karlsson et al. |
| 2001/0042584 A1 | 11/2001 | Karami et al. |
| 2002/0019615 A1 | 2/2002 | Roe et al. |
| 2002/0045881 A1 | 4/2002 | Kusibojoska et al. |
| 2002/0062117 A1 | 5/2002 | Raufman et al. |
| 2002/0065503 A1 | 5/2002 | Guidotti |
| 2002/0111596 A1 | 8/2002 | Fletcher et al. |
| 2002/0115969 A1 | 8/2002 | Maeda et al. |
| 2002/0123733 A1 | 9/2002 | Itch et al. |
| 2002/0138056 A1 | 9/2002 | Kuen et al. |
| 2002/0138062 A1 | 9/2002 | Kuen et al. |
| 2002/0156441 A1 | 10/2002 | Sawyer et al. |
| 2002/0164658 A1 | 11/2002 | Weiss et al. |
| 2002/0177829 A1 | 11/2002 | Fell et al. |
| 2003/0004490 A1 | 1/2003 | Larsson et al. |
| 2003/0014025 A1 | 1/2003 | Allen et al. |
| 2003/0022581 A1 | 1/2003 | Tsai et al. |
| 2003/0023225 A1 | 1/2003 | Sayama |
| 2003/0055394 A1 | 3/2003 | Gibbs |
| 2003/0097113 A1 | 5/2003 | Molee |
| 2003/0100878 A1 | 5/2003 | Leak et al. |
| 2003/0105443 A1 | 6/2003 | Ohnishi et al. |
| 2003/0113507 A1 | 6/2003 | Niemeyer et al. |
| 2003/0114808 A1 | 6/2003 | Underhill et al. |
| 2003/0119404 A1 | 6/2003 | Belau et al. |
| 2003/0166293 A1 | 9/2003 | Kritzman et al. |
| 2003/0199843 A1 | 10/2003 | Kato et al. |
| 2004/0044324 A1 | 3/2004 | Swenson et al. |
| 2004/0102755 A1 | 5/2004 | Morman et al. |
| 2004/0122410 A1 | 6/2004 | Itch et al. |
| 2004/0133180 A1 | 7/2004 | Mori et al. |
| 2004/0153046 A1 | 8/2004 | Ito et al. |
| 2004/0158212 A1 | 8/2004 | Ponomarenko et al. |
| 2004/0172000 A1 | 9/2004 | Roe et al. |
| 2004/0243086 A1 | 12/2004 | Van Gompel et al. |
| 2004/0243089 A1 | 12/2004 | Veith et al. |
| 2005/0003143 A1 | 1/2005 | Ducauchuis et al. |
| 2005/0027279 A1 | 2/2005 | Minato et al. |
| 2005/0075618 A1 | 4/2005 | Kenmochi et al. |
| 2005/0113778 A1 | 5/2005 | Johansson et al. |
| 2005/0131287 A1 | 6/2005 | Kaylor et al. |
| 2005/0131378 A1 | 6/2005 | Sasaki et al. |
| 2005/0143709 A1 | 6/2005 | Lindstrom |
| 2005/0148960 A1 | 7/2005 | Price |
| 2005/0175269 A1 | 8/2005 | Ashton et al. |
| 2005/0228356 A1* | 10/2005 | LaVon ............... A61F 13/505 604/385.14 |
| 2005/0256494 A1 | 11/2005 | Datta |
| 2005/0256496 A1 | 11/2005 | Benning et al. |
| 2005/0273067 A1 | 12/2005 | Malowaniec et al. |
| 2006/0024433 A1 | 2/2006 | Blessing et al. |
| 2006/0025733 A1 | 2/2006 | Kikuchi et al. |
| 2006/0036230 A1 | 2/2006 | Mills et al. |
| 2006/0047259 A1 | 3/2006 | Erdman et al. |
| 2006/0058772 A1 | 3/2006 | Karami |
| 2006/0069379 A1 | 3/2006 | Van Gompel et al. |
| 2006/0121811 A1 | 6/2006 | Mangold et al. |
| 2006/0135923 A1 | 6/2006 | Boggs et al. |
| 2006/0135928 A1 | 6/2006 | Karlsson et al. |
| 2006/0135932 A1 | 6/2006 | Abuto et al. |
| 2006/0155254 A1 | 7/2006 | Sanz et al. |
| 2006/0167424 A1 | 7/2006 | Chang et al. |
| 2006/0184149 A1 | 8/2006 | Kasai et al. |
| 2006/0212010 A1 | 9/2006 | Roe et al. |
| 2006/0241560 A1 | 10/2006 | Chang et al. |
| 2006/0247596 A1 | 11/2006 | Van Dyke |
| 2006/0258250 A1 | 11/2006 | Mangold et al. |
| 2006/0276765 A1 | 12/2006 | Swerev et al. |
| 2006/0282053 A1 | 12/2006 | Rohrl |
| 2007/0000987 A1 | 1/2007 | Karlsson |
| 2007/0003993 A1 | 1/2007 | Kritzman et al. |
| 2007/0016155 A1 | 1/2007 | Chang et al. |
| 2007/0021728 A1 | 1/2007 | Speak |
| 2007/0038199 A1 | 2/2007 | Erdman et al. |
| 2007/0044903 A1 | 3/2007 | Wisneski et al. |
| 2007/0048815 A1 | 3/2007 | Song |
| 2007/0049892 A1 | 3/2007 | Lord et al. |
| 2007/0049896 A1 | 3/2007 | Mills |
| 2007/0066950 A1 | 3/2007 | Nelson |
| 2007/0073260 A1 | 3/2007 | Roe |
| 2007/0073262 A1 | 3/2007 | Babusik et al. |
| 2007/0128589 A1 | 6/2007 | Sanders et al. |
| 2007/0208317 A1 | 9/2007 | Krautkramer et al. |
| 2007/0239131 A1 | 10/2007 | Hermansson et al. |
| 2007/0255246 A1 | 11/2007 | Schneider |
| 2007/0293833 A1 | 12/2007 | Wennerback |
| 2007/0293835 A1 | 12/2007 | Roehrl et al. |
| 2008/0026178 A1 | 1/2008 | Stupperich et al. |
| 2008/0051747 A1 | 2/2008 | Cohen |
| 2008/0086060 A1 | 4/2008 | Kritzman et al. |
| 2008/0103414 A1 | 5/2008 | Song |
| 2008/0108964 A1 | 5/2008 | Edwall |
| 2008/0125735 A1 | 5/2008 | Busam et al. |
| 2008/0134487 A1 | 6/2008 | Hartono |
| 2008/0147031 A1 | 6/2008 | Long et al. |
| 2008/0161767 A1 | 7/2008 | Sandin et al. |
| 2008/0208152 A1 | 8/2008 | Eckstein et al. |
| 2008/0249493 A1 | 10/2008 | Kobayashi et al. |
| 2008/0274014 A1 | 11/2008 | Jumonville et al. |
| 2008/0281286 A1 | 11/2008 | Petersen |
| 2008/0287897 A1 | 11/2008 | Guzman Reyes et al. |
| 2008/0287898 A1 | 11/2008 | Guzman Reyes et al. |
| 2008/0287899 A1 | 11/2008 | Morrell-Schwartz et al. |
| 2008/0312618 A1 | 12/2008 | Hundorf et al. |
| 2008/0312628 A1 | 12/2008 | Hundorf et al. |
| 2008/0312631 A1 | 12/2008 | Okuda |
| 2009/0143757 A1 | 6/2009 | Hornung et al. |
| 2009/0177176 A1 | 7/2009 | Saito |
| 2009/0198205 A1 | 8/2009 | Malowaniec et al. |
| 2009/0275071 A1 | 11/2009 | Brusilovsky et al. |
| 2009/0275911 A1 | 11/2009 | Hornung et al. |
| 2009/0299322 A1 | 12/2009 | Faulks et al. |
| 2009/0312736 A1 | 12/2009 | Schroer, Jr. et al. |
| 2009/0326503 A1 | 12/2009 | Lakso et al. |
| 2010/0051170 A1 | 3/2010 | Nakakado |
| 2010/0063468 A1 | 3/2010 | Lehto et al. |
| 2010/0065199 A1 | 3/2010 | Hornung et al. |
| 2010/0076390 A1 | 3/2010 | Norrby et al. |
| 2010/0108251 A1 | 5/2010 | Malowaniec |
| 2010/0136707 A1 | 6/2010 | Kritzman et al. |
| 2010/0163161 A1 | 7/2010 | Gilgenbach et al. |
| 2010/0168705 A1 | 7/2010 | Stabelfeldt et al. |
| 2010/0198178 A1 | 8/2010 | Litvay |
| 2010/0234820 A1 | 9/2010 | Tsai |
| 2010/0290948 A1 | 11/2010 | Song |
| 2010/0292663 A1 | 11/2010 | Lavon |
| 2010/0318055 A1 | 12/2010 | Hornung et al. |
| 2011/0071488 A1 | 3/2011 | Kuwano et al. |
| 2011/0098668 A1 | 4/2011 | Thorson et al. |
| 2011/0123775 A1 | 5/2011 | Westwood |
| 2011/0130275 A1 | 6/2011 | Weismantel et al. |
| 2011/0144610 A1 | 6/2011 | Karlson et al. |
| 2011/0146892 A1 | 6/2011 | Ostertag |
| 2011/0160692 A1 | 6/2011 | Wilkes et al. |
| 2011/0208140 A1 | 8/2011 | Roe et al. |
| 2011/0208142 A1 | 8/2011 | Roe et al. |
| 2012/0028777 A1 | 2/2012 | Knecht |
| 2012/0053552 A1 | 3/2012 | Van Gompel et al. |
| 2012/0065607 A1 | 3/2012 | Konig et al. |
| 2012/0165777 A1 | 6/2012 | Beckert et al. |
| 2012/0172828 A1 | 7/2012 | Koenig et al. |
| 2012/0310193 A1 | 12/2012 | Ostertag |
| 2013/0144245 A1 | 6/2013 | Roe |
| 2013/0211365 A1 | 8/2013 | Rajala et al. |
| 2013/0277154 A1 | 10/2013 | Fritz et al. |
| 2013/0281957 A1 | 10/2013 | Fritz et al. |

(56) References Cited

U.S. PATENT DOCUMENTS

| | | |
|---|---|---|
| 2013/0296739 A1 | 11/2013 | Schultz |
| 2013/0345657 A1 | 12/2013 | Nelson et al. |
| 2014/0046286 A1 | 2/2014 | Homann et al. |
| 2014/0121487 A1 | 5/2014 | Faybishenko et al. |
| 2015/0011958 A1 | 1/2015 | Yoshioka |
| 2015/0297421 A1 | 10/2015 | Nelson |
| 2015/0297423 A1 | 10/2015 | Nelson |

FOREIGN PATENT DOCUMENTS

| | | | |
|---|---|---|---|
| CN | 102019705 | A | 4/2011 |
| CN | 102020893 | A | 4/2011 |
| CN | 102024379 | A | 4/2011 |
| GB | 2353357 | A | 2/2001 |
| WO | 9424557 | A1 | 10/1994 |
| WO | 9734014 | A1 | 9/1997 |
| WO | 0065083 | A2 | 11/2000 |
| WO | 0065084 | A2 | 11/2000 |
| WO | 0065096 | A1 | 11/2000 |
| WO | 0065348 | A2 | 11/2000 |
| WO | 0307997 | A2 | 1/2003 |
| WO | 2004040253 | A2 | 5/2004 |
| WO | 2006017718 | A1 | 2/2006 |
| WO | 2008131904 | A2 | 11/2008 |
| WO | 2009117492 | A2 | 9/2009 |

OTHER PUBLICATIONS

Notification of Transmittal of the International Search Report and the Written Opinion of the International Searching Authority, or the Declaration; International Patent Application No. PCT/US2014/068479, Medline Industries, Inc. (Nelson, Christopher); Mar. 23, 2015.

* cited by examiner

FIG. 16

DISPOSABLE HYGIENIC ARTICLE WITH MEANS FOR DIAGNOSTIC TESTING

FIELD OF THE INVENTION

The present invention relates generally to absorbent articles and, in particular, to the use of a disposable article for collecting a sample and performing urinalysis.

BACKGROUND

Millions of people of all ages suffer from incontinence of the bowel or bladder. Whether an infant, adult, or elderly person, the underlying cause of incontinence varies but the method of treatment typically involves absorbent article products. Adult incontinent briefs, disposable diapers and underpads can alleviate some of the emotional and physical discomfort of incontinence by absorbing and containing liquid and other discharges from the human body to prevent body and clothing soiling.

Typical absorbent articles include a topsheet facing the wearer that permits fluid exudates to pass through and a backsheet that prevents the exudates from escaping from the absorbent article. Much advancement has been made in the art since the introduction of the disposable absorbent article, as shown, for example, in applicant's co-pending U.S. patent application Ser. No. 13/832,965, which is incorporated by reference herein. However, most of these articles are not adapted to aid the caregiver in the monitoring of the health of the wearer.

A problem encountered in post acute care settings is the increase in incidence of urinary tract infection ("UTI"). In addition, many patients in a managed care setting such as a nursing home require diagnostic testing. Many of these diagnostic tests require urinalysis, and many of these patients are also incontinent of urine. Therefore, collection of a urine specimen becomes a challenge for the caregivers in this environment. Current methods for collection of urine samples involve the extraction of urine from a used article. In the case of urine sampling from a baby, the sample is sometimes taken using a bag with an adhesive gasket, attaching to the wearer's skin. Finally, catheterization is sometimes used for sample collection. This practice can be attributed to an increase in incidence of UTI.

Certain attempts have been made in the art to include analysis of components of human waste, such as urine and feces, to provide indication of various specific health issues such as infections (e.g., urinary tract infections, etc.). For example, U.S. Pat. No. 5,468,236 issued to Everhart et al. on Nov. 21, 1995 discloses a disposable absorbent product that includes a chemically reactive means having an end point adapted to provide a visual indicator of the presence of a substance in mammalian bodily excrement. In another example, U.S. Pat. Nos. 7,365,238 and 8,217,217 issued to Diehl et al. on Apr. 29, 2008 and Jul. 10, 2012, respectively, disclose wearable articles with the capability to detect signals related to a dehydrated state of a wearer. However, the prior art fails to provide the caregiver with a convenient means of collecting samples and conducting a urinalysis.

Accordingly, a need exists for absorbent articles that provide a wearable article that can provide diagnostic functionality.

BRIEF DESCRIPTION OF THE DRAWINGS

The foregoing and other advantages of the invention will become apparent upon reading the following detailed description and upon reference to the drawings.

The drawings listed above are intended to convey to one of ordinary skill in the art the present invention and its embodiments. In some drawings certain elements have not been shown for clarity. While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Absorbent articles as described herein generally include a moisture-pervious inner layer, an absorbent layer, and a moisture-impervious outer layer. Although the remainder of the description will be specifically directed to adult incontinence articles, such as disposable diapers, it is to be understood that the embodiments may also be implemented using other absorbent articles and that the properties and uses described below apply to these other absorbent articles as well. Throughout this application, the terms absorbent article and diaper are used interchangeably. However, it should be understood that the term diaper is intended to include other absorbent articles, such as training pants, incontinence pads, etc., as would be understood by one of ordinary skill in the art.

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, proximal and distal, and the like may be used solely to distinguish one entity or action from another entity or action without necessarily requiring or implying any actual such relationship or order between such entities or actions.

Figure 1:
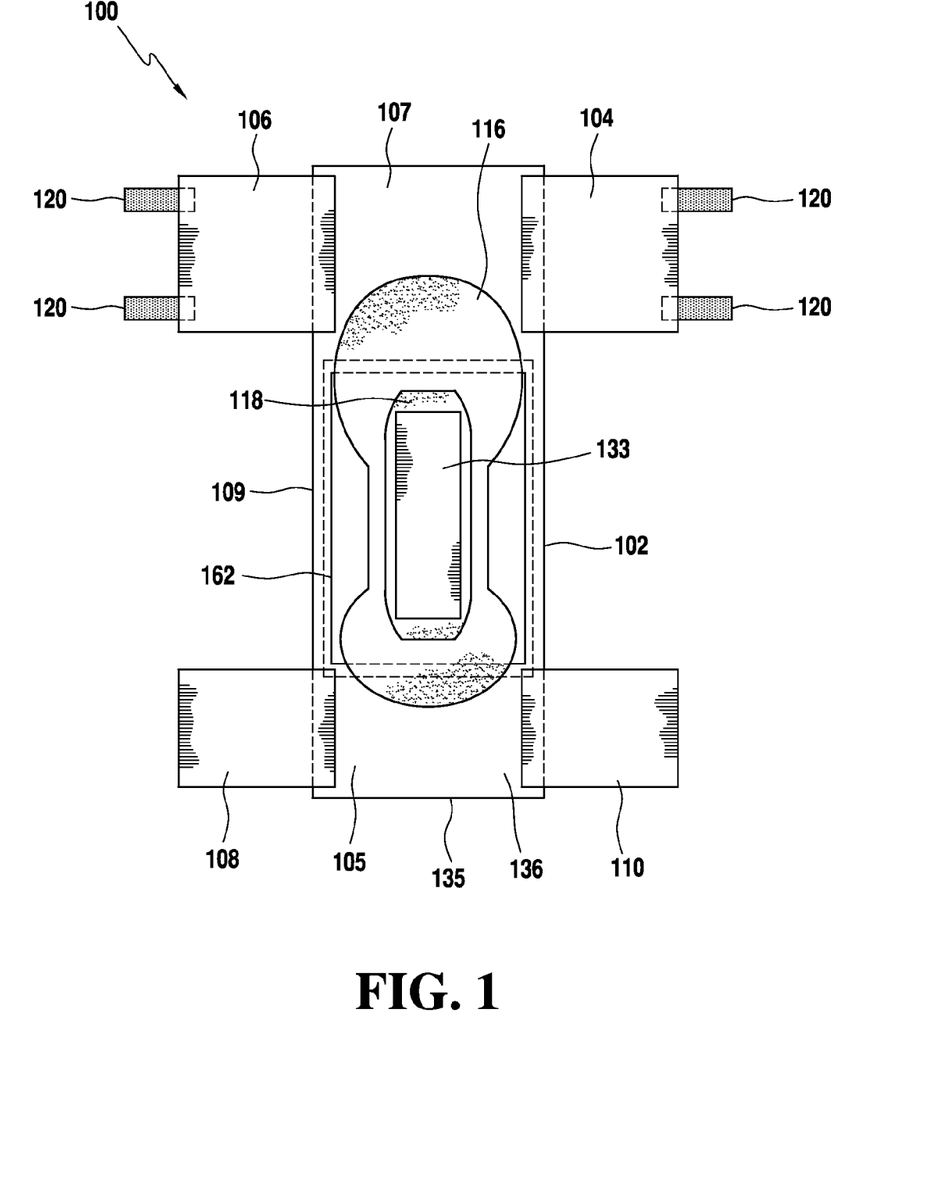
FIG. 1 is a top plan view of an absorbent article in a substantially flat un-contracted position according to one embodiment of the invention.
Figure 2:
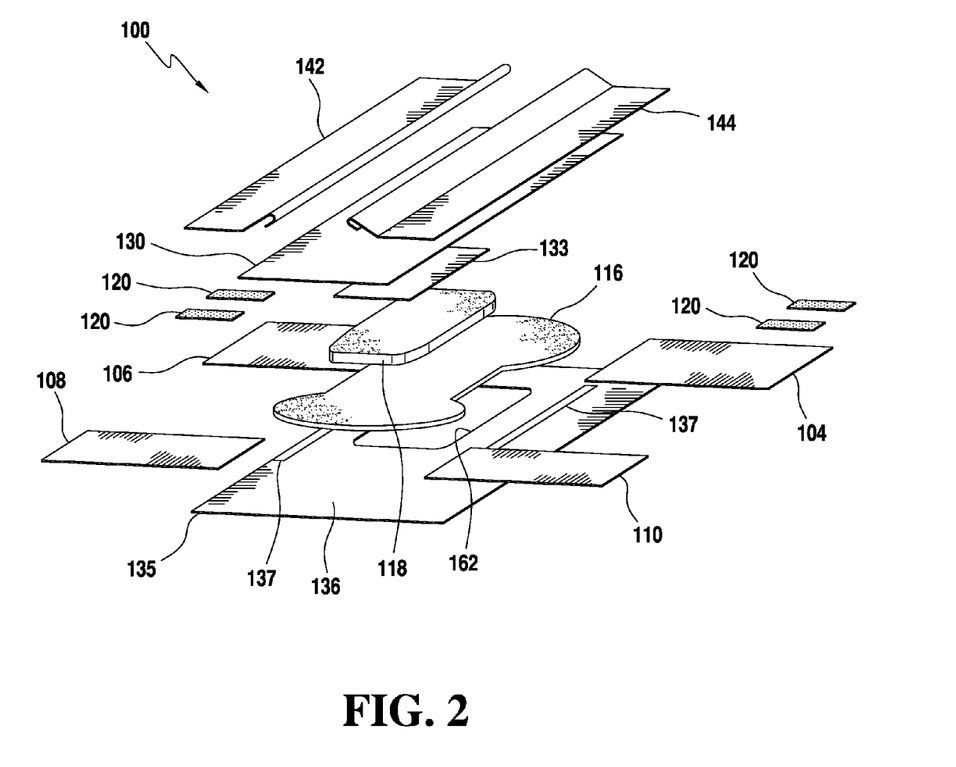
FIG. 2 is an exploded perspective view of the absorbent article of FIG. 1, again in a substantially flat un-contracted position.

FIGS. 1 and 2 illustrate an exemplary non-limiting general embodiment of an absorbent article 100. FIG. 1 illustrates a plan view of the absorbent article 100 in a substantially flat un-contracted state. As shown in these figures, the absorbent article 100 generally consists of several layers, including an inner layer, an absorbent layer, and an outer layer. The inner layer faces a wearer and contacts the skin of the wearer when the absorbent article 100 is secured to the wearer. The inner layer may comprise a topsheet 130 that is composed of a moisture-pervious fabric suitable to allow bodily discharge to pass through the inner layer and be absorbed by the absorbent layer. Non-limiting examples of materials suitable to form the topsheet 130 include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

The plan view of FIG. 1 is shown from the top or patient contacting side of the absorbent article. The topsheet (130) and other components have been removed for clarity. FIG. 2 is an exploded perspective view of the absorbent article 100. Again, the article 100 is shown in a substantially flat un-contracted state with certain items removed for clarity.

As shown in FIG. 1, an embodiment of the absorbent article 100 comprises a chassis 102. The chassis 102 includes a front waist region 105, a back waist region 107, and a crotch region 109 that is disposed longitudinally between the front and back waist regions 105 and 107. The front waist region 105 and the back waist region 107 generally comprise those portions of the absorbent article 100 which, when worn, encircle the waist of the wearer. The crotch region 109 is that portion of the absorbent article 100 which, when the absorbent article 100 is worn, is generally positioned between the legs of the wearer.

The chassis 102 has a shape such that its outer perimeter is rectangular or at least substantially rectangular in the illustrative embodiment of the absorbent article 100. In other embodiment, there may be portions of the chassis that are shaped and/or removed, such as in the crotch region 109, for example, resulting in a narrower crotch region portion 109 to provide a contoured fit between the legs. Still other embodiments have different shaped chassis, such as hourglass shapes, T-shapes, and the like.

Rear side panels 104, 106 are coupled to and may extend from the back waist region 105. The disposable article may further include front side panels 108, 110 that are coupled to and may extend from the front waist region 105. The back region 107 is generally positioned against the back of the user. The front region 105 is generally positioned against the front of the user. The rear side panels 104, 106 are configured to wrap around a wearer's waist from back to front, extending from each side of the back waist region 105. The front side panels 108, 110 are configured to wrap around a wearer's waist from front to back. In this manner, rear side panel 106 can be connected to front side panel 108 and rear side panel 104 can be connected to front side panel 110 to couple the front region 105 to the back region 107. In this embodiment there are four side panels 104, 106, 108, 110. However, it should be recognized that other embodiments may be configured with more or fewer side panels. In particular, rear side panels 104, 106 may connect directly to an outside surface of front waist region 105 rather than to front side panels 108, 110.

The side panels may attach to the chassis 102 in a variety of manners as would be apparent to one of skill in the art. For example, as described in applicant's co-pending U.S. patent application Ser. No. 13/832,965. Alternatively, one or more of the side panels may be integrally formed, in whole or in part, with a backsheet 135 or topsheet 130 of the absorbent article. The backsheet 135 will have an outside surface 134 facing away from the patient wearing the absorbent article and an inside surface 136 facing toward the patient.

The rear side panels 104, 106 may also include fasteners 120. Fasteners 120 may comprise adhesive tape, hook and loop, snaps or any other appropriate fasteners as would be understood by one of ordinary skill in the art. As shown in the illustrative embodiment, rear side panel 104, 106 includes two fasteners 120. In a preferred embodiment, fasteners 120 can be configured to operatively couple rear side panels 104, 106 to a front region 105 of the diaper chassis 102. Alternative, fasteners 120 may also engage front side panels 108, 110 to attach rear side panels 104, 106, respectively. While FIG. 1 depicts rear side panels 104, 106 as including two fasteners 120, in some embodiments, more or fewer fasteners may be used. While FIG. 1 depicts fasteners 120 sized and shaped a particular way, in other embodiments, fasteners 120 can be a different size and/or shape. Alternatively, the front side panels 108, 110 may include fasteners in additions to, or in place of, the fasteners 120 attached to rear side panels 104, 106.

In another embodiment, the front region 105 and/or front panels 108, 110 may include added or modified features to reinforce or increase the affinity to the fastening device. Additionally, features may be employed to allow adhesive fasteners to be attached and detached from the fastening region multiple times. Those skilled in the art will recognize that there are multiple approaches to doing so via modification of the base material as well as additions of various materials. For example, fasteners 120 may incorporate the hook component of a hook-and-loop closure and portions of the front region 105 and/or front panels 108, 110 may be comprise a corresponding loop component. The surface of front region 105 and/or front panels 108, 110 may be treated to increase or decrease the affinity for the hook components. Alternatively, separate loop component material may be adhered to the surface of the front region 105 and/or front panels 108, 110.

Referring again FIGS. 1 and 2, embodiments of the absorbent article 100 include an absorbent layer. The absorbent layer may comprise an acquisition and/or distribution ("A/D") layer 133, a first absorbent core 116, and a second absorbent core 118.

The liquid acquisition and/or distribution layers serves to rapidly acquire and then distribute acquired liquid to an absorbent core for retention. To achieve rapid acquisition and distribution, these layers often include cellulosic fibers. These layers can include cross-linked cellulosic fibers to impart bulk and resilience to the layer, and wood pulp fibers to increase the wicking of liquid within the layer and to facilitate distribution of the liquid throughout the layer and ultimately to another layer, such as a storage layer, that is in liquid communication with the distribution layer.

Figure 3:
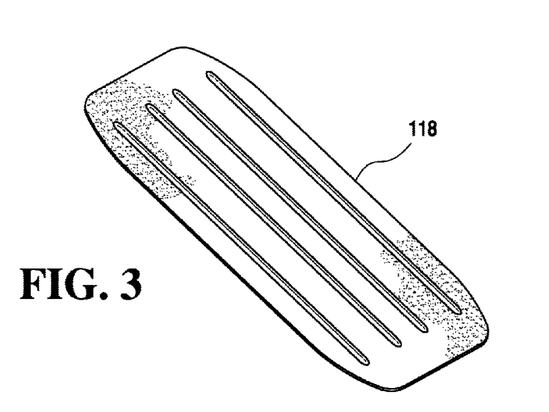
FIG. 3 is a perspective view of a second absorbent core of the absorbent article depicted in FIG. 1.
Figure 4:
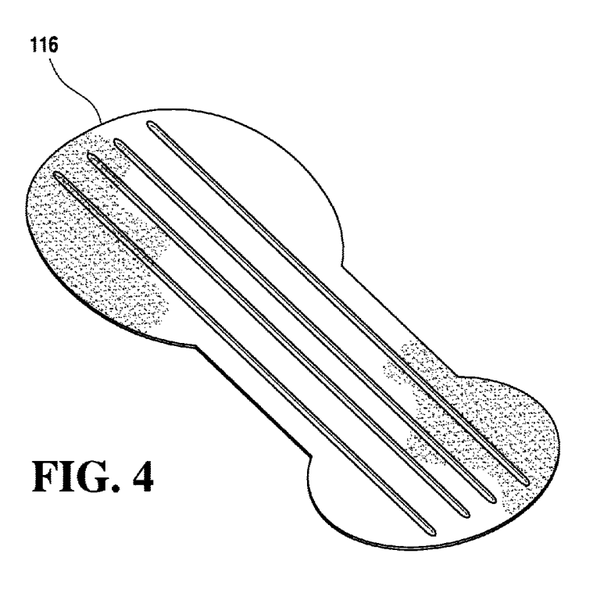
FIG. 4 is a perspective view of a first absorbent core of the absorbent article depicted in FIG. 1.

FIG. 3 is a perspective view of a top (facing towards wearer) of the second core 118, and FIG. 4 is a perspective view of a bottom side (facing away from a wearer) of the first core 116. Each of the first core 116 and second core 118 can be composed of similar material, and can be shaped depending on the size of the absorbent article, and whether it is intended for use by infants, children and/or adults. By way of example, and as shown in FIGS. 3 and 4, first core 116 can be larger and substantially hourglass shaped, whereas second core 118 can be smaller, relative to first core 116, and can be substantially rectangular shaped. In this manner, the absorbent article can include a large surface area of coverage provided by the first core 116, and the increased absorbency provided by the second core 118, without the additional bulk of a second core having the same size as the first core.

First core 116 is shown having an embossed bottom and second core 118 is shown having an embossed top. The embossed top of second core 118 and the embossed bottom of first core 116 provide increased longitudinal flow while reducing lateral flow, and, in this manner, reducing leakage. Said another way, the embossed top of second core 118 and the embossed bottom of first core 116 allows fluid to move longitudinally towards the front and the back of a wearer, as opposed to towards the legs of a wearer.

Each of the first core 116 and the second core 118 may be composed of any materials suitable for absorbing the fluids and discharge including, but not limited to, a fibrous material (e.g., fluffed wood pulp), a super absorbent polymer ("SAP"), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper may vary depending upon whether it is intended for use by infants, children and/or adults.

While FIGS. 3 and 4 depict the first core 116 having an embossed bottom, and the second core 118 having an embossed top, in some embodiments, an absorbent article can have only a single core with no embossing, a single core with embossing on both, and/or other combinations of one or two cores each with embossing on one, both, or neither side. While the figures show absorbent articles include one or two cores, in some embodiments, absorbent articles can include more or fewer cores.

FIGS. 3 and 4 depict embossing as including four spaced apart embossing "lines," in some embodiments. However, a core can include more or fewer embossing lines. In some embodiments, embossing lines can be adjacent one another, or can be a combination of adjacent and space apart embossing line. In this manner, the different combinations of embossing lines can define an embossing pattern. While FIGS. 3 and 4 depict embossing substantially along the entire width and length of each respective core, in some embodiments a core can have embossing substantially along an entire width and/or length, and/or a portion of a width and/or length.

In embodiments of the invention, the first 116 and second 118 cores may be created with or without the use of super absorbent polymer (SAP). While some literature indicates that the presence of SAP in a diaper used for urine testing is considered benign, manufacturing diapers without SAP for the benefit of accuracy is contemplated by the present invention and may be considered beneficial.

Returning to FIGS. 1 and 2, the absorbent article 100 may further include a set of leak guards and/or a set leg cuffs 142, 144, both known to those of ordinary skill in the art. Additionally, the exemplary absorbent article includes an outer layer or backsheet 135 and elastic bands 137. The elastic bands 137 can by used to gather the leg of the article around the user's leg, improving the fit of the absorbent article 100 and can improve the comfort of the wearer. Elastic bands and other elastic materials may be used at other places in the absorbent article in order to improve the fit and/or fluid retention of the article.

Figure 5:
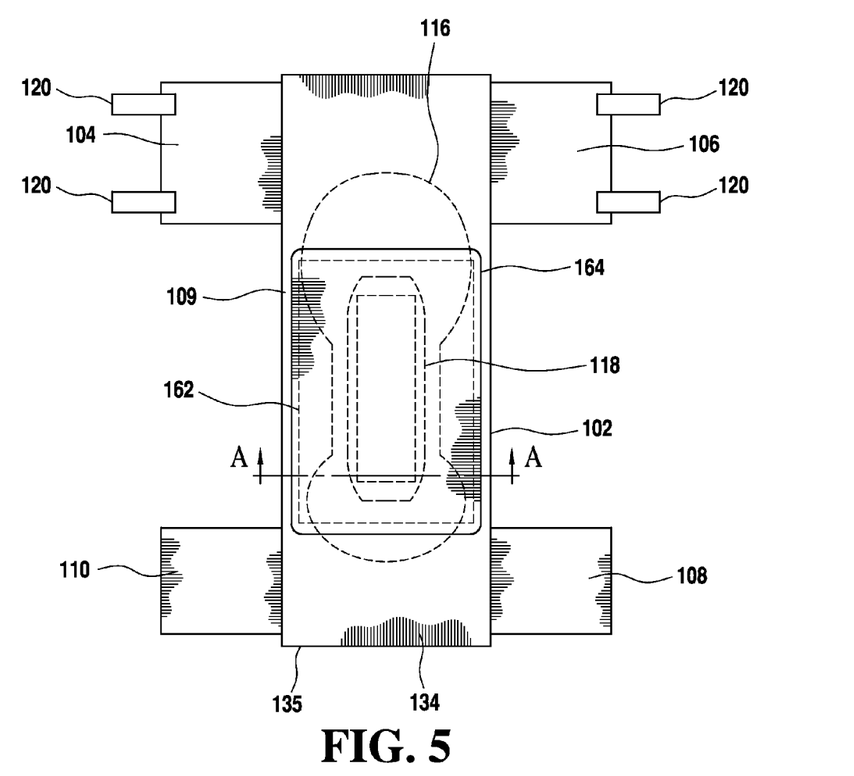
FIG. 5 is a perspective view of an absorbent article in accordance with an embodiment of the invention as viewed from an underside of the article.

In further embodiments of the invention, the absorbent article includes a window or test port 162. The test port 162 passes through the backsheet 135 creating a through opening in the backsheet. As shown in FIG. 5, the test port 162 may have a cover 164 that surrounds the test port. The test port may be positioned in the crotch region 109 of the chassis 102 and may extend under at least a portion of the first absorbent core 116 and a portion of the second absorbent core 118. Alternatively, the test port may be position entirely or partially in the front 105 or back 107 waist regions.

Figure 6:
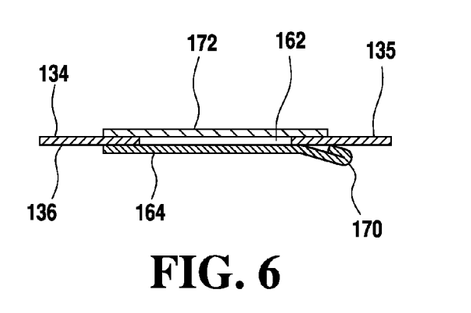
FIG. 6 is a section view of a test port and cover in accordance with an embodiment of the invention.

As illustrated in FIG. 6, a section of the backsheet 135 is removed to form the test port 162. A cover 164 may be placed on the outside surface 134 of the backsheet surrounding the test port 162 so as to completely cover the test port. The cover may be releasably adhered to the backsheet.

The combination of the test port and cover allows the caregiver to collect and/or analyze a sample of urine that has collected in the absorbent article without the need to remove the article from the patient. Embodiments of the invention can be utilized with commercially available test strips, including but not limited to, for the identification of nitrites, ketones, proteins, pH level, hormone, Leukocytes, Bilirubin, Blood, Urobilinogen, and specific gravity. These indicators can aid in providing information about carbohydrate, metabolism (diabetes), kidney health, pregnancy, occult blood, acid/base balance, leukocytes (infection) and other health related conditions. In addition, embodiments of the invention may benefit the care facility by separating the storage conditions of the diaper from storage conditions of the test strip, thereby improving the shelf life and performance of the reagent strip.

Once inserted into the test port area 162 of the article 100, the reagent strip is utilized in the same manner as the strip would be when deployed in a traditional fashion (e.g., mid-stream sample collection into a cup).

The cover 164 may be of any appropriate, liquid impermeable material. For example, the cover may be formed of the same material as the backsheet 135. Alternatively, the cover 164 may be formed from a clear or translucent film or may comprise one or more clear portions. Use of a transparent material may allow the caregiver to place the test strip within the test port 162, return to the patient after the patient has voided, and read the strip (by comparison of the color chart to the reagent strip) without handling the strip or extracting urine from a diaper.

The cover 164 may comprise a finger lift 170 that aids the user in opening the cover 164. The finger lift 170 comprises a portion of the cover that is not adhered directly to the outside 134 of the backsheet 135. Additional embodiments may include a die cut or shaped tab. The caregiver can, accordingly, more easily grasp an edge of the cover 164 to peel the cover back from the backsheet, thereby opening the test port 162. The finger lift 170 may comprise a portion of the cover that is folded over upon itself to create a non-adhesive area at an edge of the cover.

In a further embodiment, the cover 164 may comprise a wetness indicating feature (not shown). The wetness indicator may include graphics, symbols, figures, writing or any other indicator comprised of color changing hotmelt adhesive, color changing ink, dissolving ink, or other means of indicating that the area has been exposed to an insult—as a result of urination—or that the area has been exposed to an insult for a sufficiently long duration of time for the reagent strip to function. In additional embodiments, graphics may be included in test port without the use of a wetness indicator.

Figure 10:
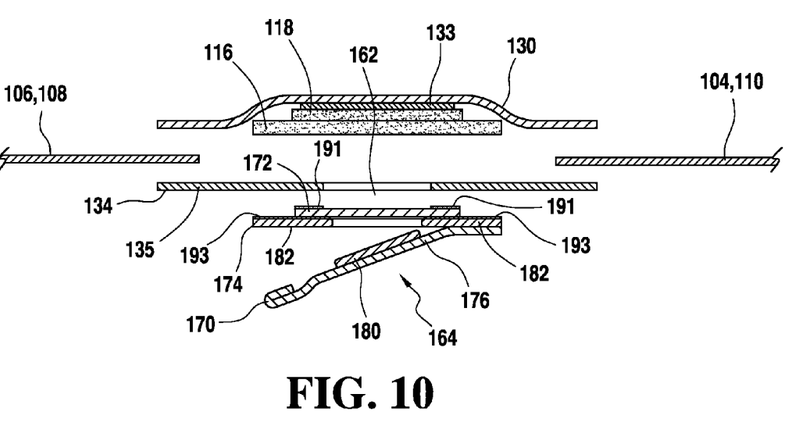
FIG. 10 is a cut-away side view of an absorbent article in accordance with the present invention.

In addition, embodiments of the absorbent article may comprise a separation layer 172 that separates the absorbent cores 116, 118 from the cover 164. This separation layer 172 provides a barrier so that absorbent fluff is not exposed to the caregiver while inserting the test strip. The separation layer may be a nonwoven material. More particularly, the separation layer may be a hydrophilic nonwoven material. The separation layer may be positioned such that its edges overlap with the inside surface 136 of the backsheet 135, as shown in FIG. 6. Alternatively, the separation layer 172 may be positioned such that its edges overlap with the outside surface 134 of the backsheet 135, as shown in FIG. 10. In such an embodiment, an adhesive layer 191 may be applied in a window frame shape around the perimeter of the separation layer 172 in order to adhere the separation layer 172 to the backsheet 135. Additionally, the separation layer 172 may form part of the cover structure 164 as shown in FIG. 8.

Figure 7:
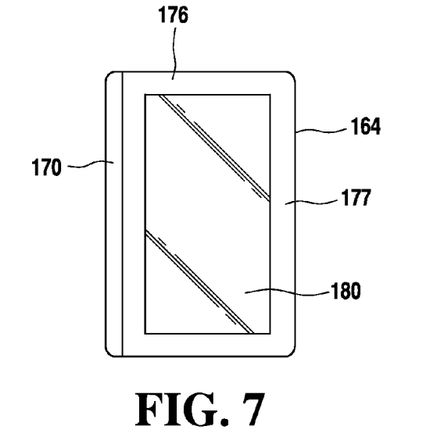
FIG. 7 is a plan view of the patient facing side of a cover for a test port of an embodiment of the invention.
Figure 8:
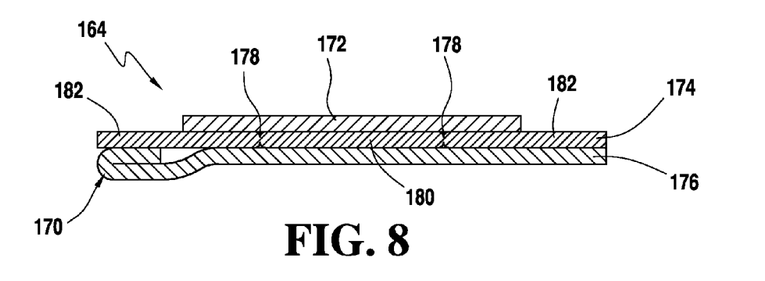
FIG. 8 is a cut-away side view of further embodiment of a test port cover with the cover in a closed position.
Figure 9:
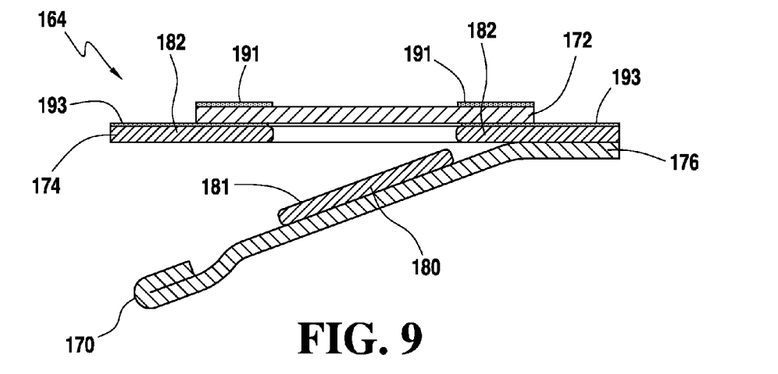
FIG. 9 illustrates the embodiment of FIG. 8 with the cover in an open position.

As illustrated in FIGS. 7-9, embodiments of the cover 164 may comprise several components. FIGS. 7-9 illustrate a cross-section of the cover 164 generally along section line A-A of FIG. 5. Embodiments of the cover 164 include a separation layer 172 as described above. This separation layer 172 may be placed so that the edges overlap the outside surface 134 of the backsheet 135, surrounding the test port 162. The cover structure 164 may also include a base layer 174. The base layer 174 may overlap with both the separation layer and the backsheet outside surface 134 and be adhered to the backsheet 135 and/or separation layer 172 by a layer of adhesive 193 in a window frame shape around the perimeter of the base layer 174. In embodiments of the invention, the base layer 174 may comprise a bi-axially oriented polypropylene ("BOPP") film. The cover 164 may further include an outer layer 176. The outer layer may cover, and be adhered to, out outer surface of the base layer 174. The outer layer may include a finger lift 170. Other films may also be used for the test port, including those used in packaging of food products, and may use low-tack, resealable adhesives.

The base layer 174 may include die cuts 178 extending through the base layer. In this manner, as the cover is pealed back using the finger lift 170, the base layer 174 separates into two parts, a central portion 180 that remains connected to the outer layer 176 and a peripheral portion 182 that remains attached to the backsheet 135. The base layer 174 may include a layer of film 181 applied to at least a portion of its top surface and extending at least over the central portion 180. This film, which may be a clear film, prevents the central portion of the base layer 174 from adhering to the separation layer 172. The caregiver may thereby access a test port within the absorbent article where a test strip can be placed.

The region 177 on an inside surface of the cover 164 surrounding the central portion 180, as illustrated in FIG. 7, may be an adhesive layer used to releasably attach the outer layer 176 of the cover 164 of the test port 162 to the base layer 174. The base layer 174 is attached to the backsheet via a "picture frame" configuration of hotmelt adhesive 193 applied to a peripheral portion 182. Generally, this type of adhesive pattern is applied through the use of a hot melt application (slot coat) nozzle where the adhesive can be selectively turned on or off in prescribed regions across the width of the applicator.

Because the base layer 174 is only adhered to the backsheet in the outside perimeter 182, the center 180 of layer 174 may be torn away or deployed when peeling the outer layer 164 away as shown in FIG. 9. A die cut 178, which does not completely sever the layer, may be made through base layer 174 to allow the center portion 180 to separate with the cover 176 when the outer layer 176 is pulled away.

FIG. 10 illustrates an absorbent article having a test port according to embodiments of the invention. For clarity, certain elements that may be used in the article have not been illustrated in FIG. 10, for example leg cuffs 142, 144, among others. The exemplary diaper shown in FIG. 10 includes a topsheet 130. The topsheet is positioned above an A/D layer 133. The article may further include a first absorbent core 116 and a second absorbent core 118. A backsheet 135 having a test port 162 extending therethrough is positioned beneath at least a portion of the absorbent core 116. A separation layer 172 is positioned to cover the test port 162. The test port and separation layer are in turn covered by a cover 164 comprising a base layer 174, having a central portion 180 and a peripheral portion 182, and an outer layer 176. The outer layer 176 may include a finger lift 170. The diaper may also include side panels 104, 106, 108, 110 that attach to the topsheet 130 and/or the backsheet 135 and extend from the lateral edges of the chassis.

Manufacturing of embodiments of the present invention will include those steps employed in manufacturing an absorbent article as would be understood by one of ordinary skill in the art with the addition of those steps necessary to create a test port.

Figure 11:
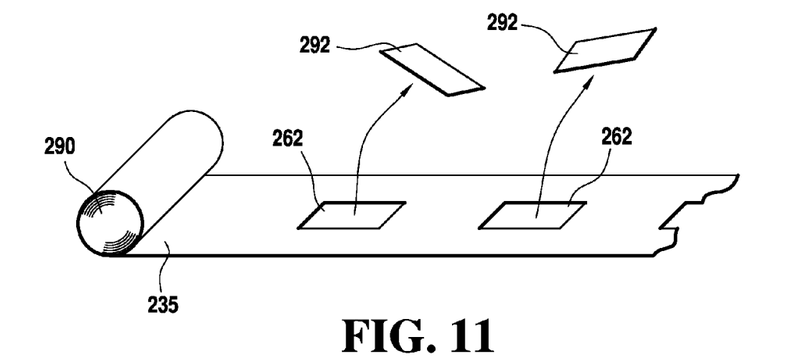
FIGS. 11-16 are representative diagrams illustrating steps in an embodiment of a manufacturing process for manufacturing an absorbent article.

In a first process, as shown in FIG. 11, a film of backsheet material 235 is unrolled from a roll 290. A section of the film 292 is removed from the backsheet 235, leaving an aperture 262 in the film. The removed sections 292 are discarded or recycled as waste.

Figure 12:
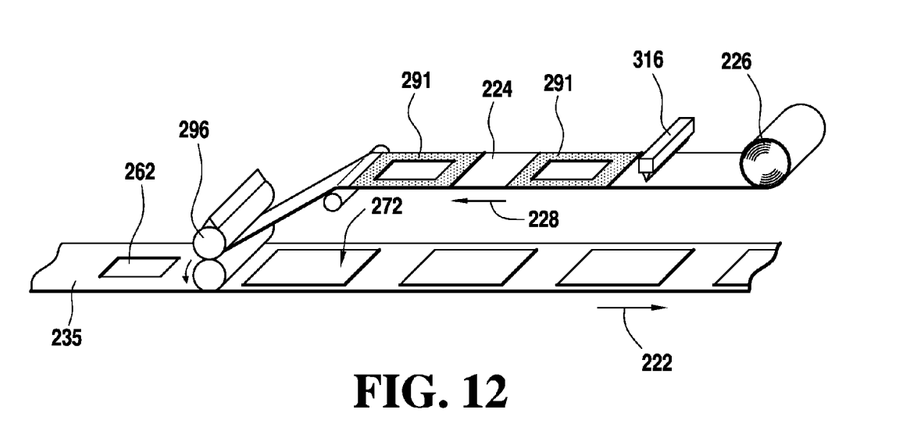

In a further step of the processes, as illustrated by FIG. 12, the backsheet 235 moves along a processing line in a direction shown by arrow 222. A web of permeable material 224 is unrolled from a second roll 226 in the direction show by arrow 228. The permeable material 224 may be a hydrophilic nonwoven material. An adhesive applicator 316 applies a window frame shaped adhesive pattern 291 to the permeable material 224. Sections of the nonwoven material are slip cut from the web of material 224 by a rotary cutter 296 and placed on the backsheet 235 to form nonwoven separation patches 272 such that the window frame adhesive 291 adheres the separation patches 272 around the periphery of apertures 262 in backsheet 235. Alternatively, permeable material 224 could be continuously applied in the same length as the backsheet 235 for simplification of the process.

Figure 13:
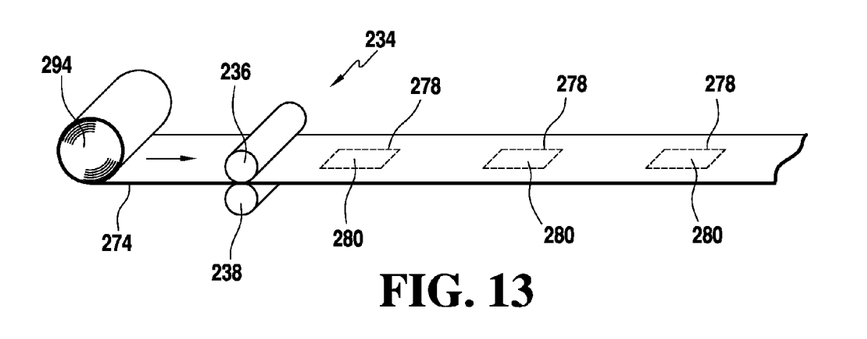

In a second process, as illustrated by FIG. 13, a base layer 274 is unrolled from a roll of film material 294. A rotary die 234, including an anvil 236 and a pattern die 238, creates a perforated cut 278 through the base film 274, which creates a central portion 280 but does not completely sever the layer.

Figure 14:
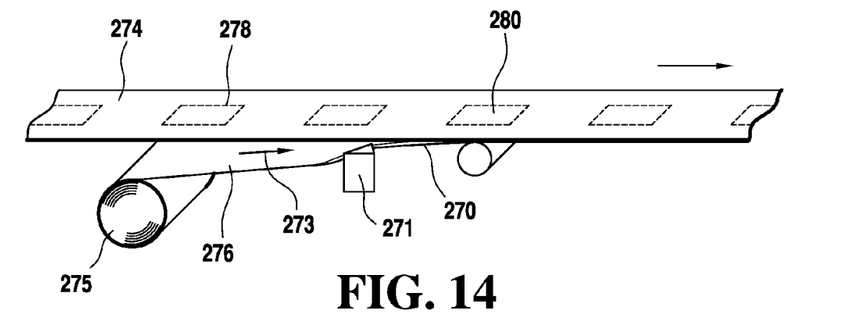

FIG. 14 illustrates a further step of the second process in which a web of an outer layer of material 276 is unwound from a roll 275 such that the outer layer is moving in a direction 273 while the base layer material 274 continues to move along the processing line. A fold 271 is applied to an edge of the outer layer 276 in order to create a finger lift fold 270. The outer layer of material 276 is adhered to an outer surface of the base layer 274.

Figure 15:
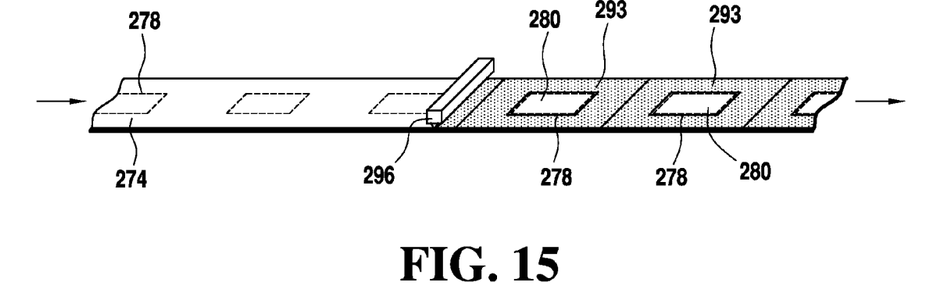

FIG. 15 illustrates an additional step of the second process in which an adhesive applicator 296 applies a window frame shaped layer of adhesive 293 to the base layer 274 surrounding die cuts 278 and center portions 280.

Figure 16:
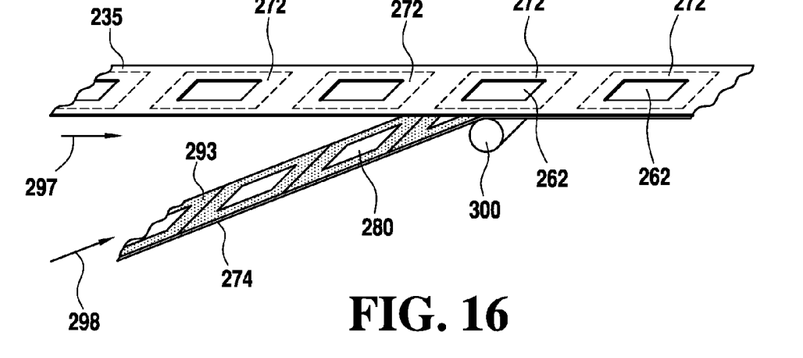

As illustrated in FIG. 16, the backsheet 235 with separation patches 272 as produced by the first process, shown in FIGS. 11-12, moves in a direction illustrated by arrow 297. The base layer material 274 produced by the second process, shown in FIGS. 13-15, moves in a direction illustrated by arrow 298. The base layer material 274 moves through a slip/cut unit 300 that cuts the base layer material 274 and places it as discrete cover structures on an outer surface 234 of the backsheet 235 over the separation patches 272 and apertures 262 in the backsheet 235.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. An absorbent article, comprising:
   a liquid pervious topsheet having a proximal surface facing toward a user when the article is in use and a distal surface facing away from the user;
   an absorbent material positioned distally from the topsheet and extending across at least a portion of the topsheet distal surface;
   a liquid impervious backsheet positioned distally from the absorbent material and topsheet, the backsheet comprising a through aperture having a perimeter;
   a cover positioned on a surface of the backsheet and covering the backsheet aperture; and
   a separation layer non-releasably attached to the backsheet and extending at least partially across the backsheet aperture between the cover and the absorbent material;
   wherein the cover is releasably attached to the backsheet such that the backsheet aperture may be selectively uncovered without removing the absorbent article from the user.

2. The absorbent article of claim 1, wherein the separation layer comprises a porous non-woven material.

3. The absorbent article of claim 2, wherein the non-woven material is hydrophilic.

4. The absorbent article of claim 1, wherein the cover comprises a liquid impervious outer layer.

5. The absorbent article of claim 4, wherein the cover comprises a finger lift portion.

6. The absorbent article of claim 5, wherein the finger lift portion is formed by folding the outer layer upon itself along an edge of the cover.

7. The absorbent article of claim 4, wherein the cover further comprises a base layer positioned between and overlapping with at least a portion of the cover outer layer and a portion of the backsheet.

8. The absorbent article of claim 7, wherein the cover comprises a transparent material.

9. The absorbent article of claim 4, wherein the cover comprises a wetness indicator.

10. The absorbent article of claim 1 further comprising a resealable adhesive positioned between the cover and the backsheet.

11. The absorbent article of claim 1, wherein the backsheet aperture is a test port.

12. The absorbent article of claim 11, wherein the test port is adapted to accommodate placing an analysis device into the test port.

13. The absorbent article of claim 12, wherein the cover is adapted to close over the test port.

14. The absorbent article of claim 1, wherein the separation layer extends across the entire backsheet aperture.

15. The absorbent article of claim 1, wherein the separation layer is adhered to the backsheet around the entire perimeter of the backsheet aperture.

16. The absorbent article of claim 1, wherein the separation layer is intermittently adhered to the backsheet around the entire perimeter of the backsheet aperture.

17. The absorbent article of claim 16, wherein the separation layer is attached to the backsheet by an adhesive.

18. The absorbent article of claim 16, wherein the adhesive comprises an adhesive layer applied in a window frame shape around a perimeter of the separation layer.

19. The absorbent article of claim 16, wherein the cover comprises a base layer non-releasably attached to the backsheet and an outer layer releasably attached to the base layer.

* * * * *